United States Patent [19]

Comyns et al.

[11] Patent Number: 4,622,214

[45] Date of Patent: Nov. 11, 1986

[54] METHOD FOR THE PREPARATION OF CRYSTALLINE MOLECULAR SIEVE MATERIALS WHEREIN THE ORGANIC TEMPLATE IS AN ENANTIOMER

[75] Inventors: Alan E. Comyns, Chester; Gareth W. Morris, Wirral; John P. Sankey, Great Sankey Warrington, all of England

[73] Assignee: Laporte Industries Limited, London, England

[21] Appl. No.: 796,193

[22] Filed: Nov. 8, 1985

[30] Foreign Application Priority Data

Nov. 17, 1984 [GB] United Kingdom ................. 8429121
Apr. 2, 1985 [GB] United Kingdom ................. 8508619

[51] Int. Cl.$^4$ ............................................ C01B 35/10

[52] U.S. Cl. ..................................... 423/277; 423/326; 423/328; 423/329; 423/330; 423/335; 423/339; 423/331; 423/332; 502/60; 502/61; 502/62; 502/64; 502/66; 502/77; 502/202; 502/78

[58] Field of Search ....................... 423/328, 329, 326; 502/60, 77, 202

[56] References Cited

U.S. PATENT DOCUMENTS 4,108,881 8/1978 Rollmann et al. .................... 502/62

Primary Examiner—John Doll
Assistant Examiner—Jackson Leeds
Attorney, Agent, or Firm—Kane, Dalsimer, Kane, Sullivan and Kurucz

[57] ABSTRACT

Crystalline molecular sieve materials such as high silica zeolites are manufactured using an organic template comprising an optically active enantiomer such as an enantiomer of 3($\pm$) methyl piperidine -N,N-dimethyl bromide.

A new zeolite materials is identified.

5 Claims, 5 Drawing Figures

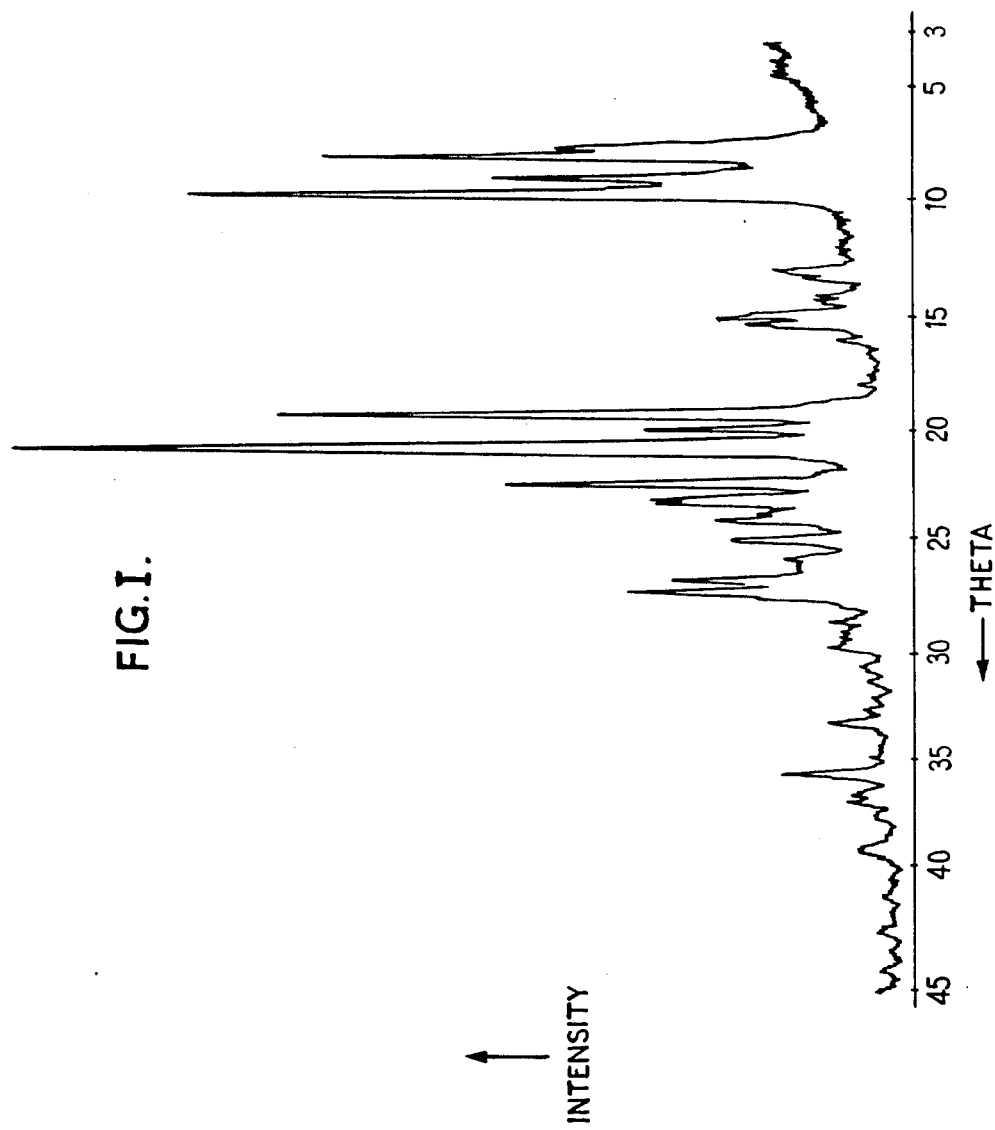
FIG. I.

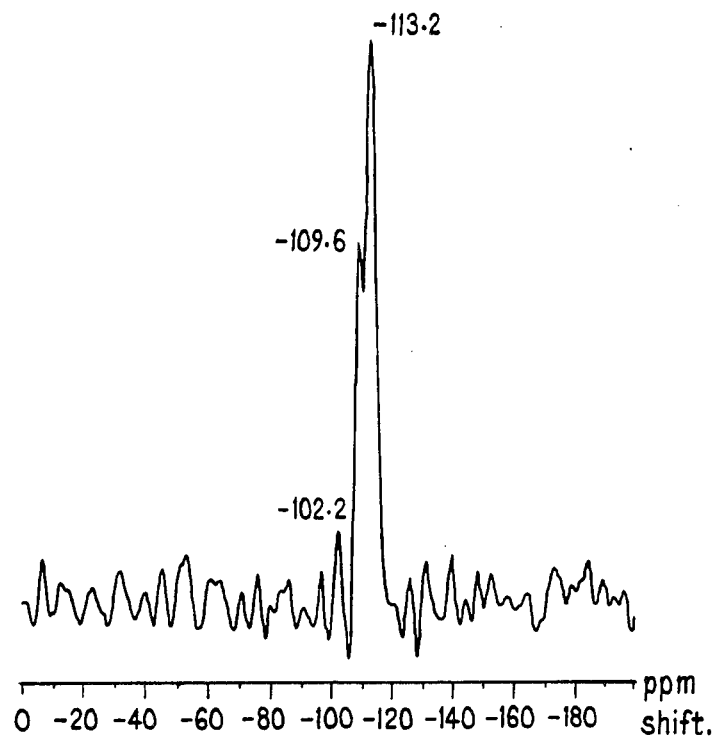
FIG. II.

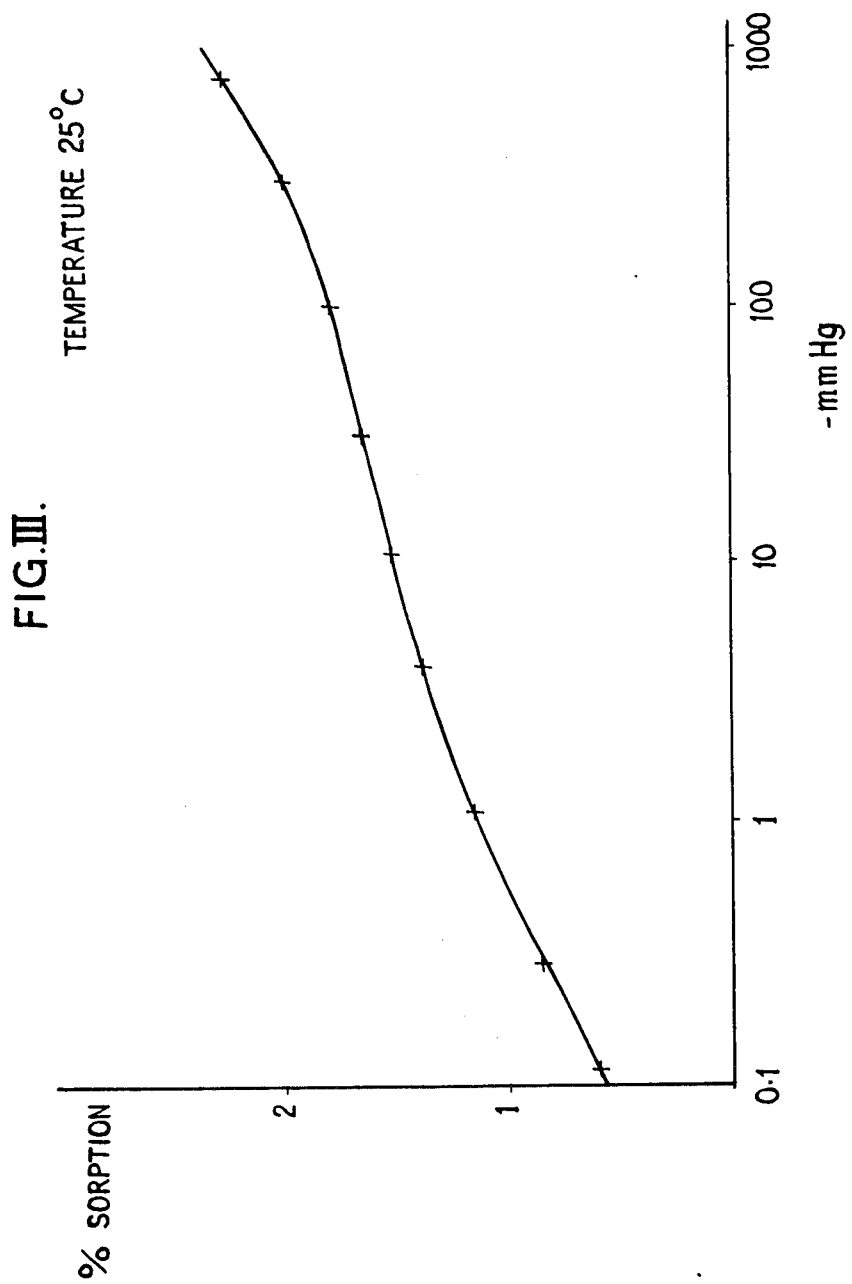
FIG. III.

FIG. IV
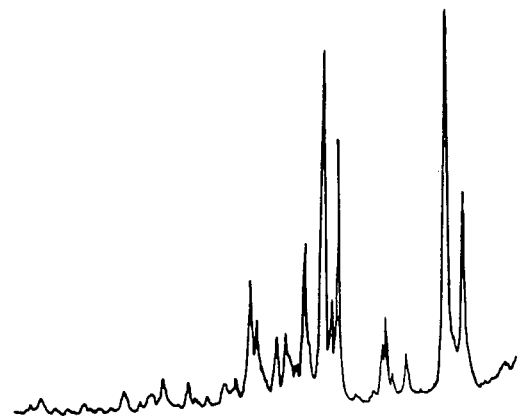
FIG. V
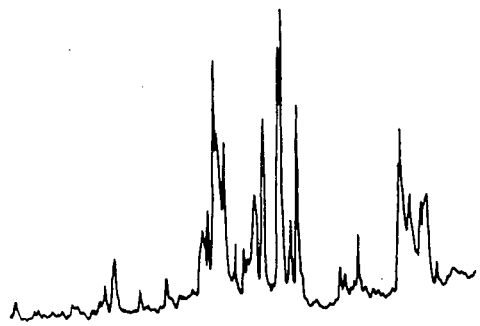

METHOD FOR THE PREPARATION OF CRYSTALLINE MOLECULAR SIEVE MATERIALS WHEREIN THE ORGANIC TEMPLATE IS AN ENANTIOMER

BACKGROUND OF THE INVENTION

1. Field of the Invention

This invention relates to a novel process for the preparation of crystalline, synthetic molecular sieve materials and materials so produced.

2. Summary of the Invention

By 'molecular sieve' is meant herein microporous three dimensional framework materials having pores generally in the 2 to 20 Angstroms size range which are capable of use for molecular separations. The framework may consist of or comprise, for example, aluminosilicate, aluminophosphate or silica.

According to one aspect of the present invention there is provided a process for the production of a synthetic crystalline molecular sieve material characterised by the use in the reaction mixture of an organic template comprising an optically active enantiomer. It has now been found that by the use of the novel templates described above the synthesis may be controlled to produce different products than would be produced using the corresponding racemic form of the template and that novel zeolites may be produced thereby.

The present invention is particularly, although not exclusively, concerned with the preparation of high silica zeolites or their silica analogues. By "high silica zeolite" is meant a zeolite having the general formula:

$$xR_2O:yM_2O_3:zSiO_2:wH_2O$$

where R is one or more alkali metal or alkaline earth metals of valency n preferably sodium, $M_2O_3$ is an oxide of one or more of B, Al, V, Cr, Mn, Fe, Ga, As, Mo or Sb but preferably Al, x is a charge balancing quantity of R, y is from 0 to 1, z is more than 6, for example from 10 to 5000 and W is at least 0 for example from 0 to 2000. While zeolites having a lesser content of silica such as the traditional zeolites A, X and Y may be manufactured readily without the assistance of an organic template material high silica zeolites are generally synthesised with the assistance of an organic template material present in the reaction medium. Such synthesis may be accomplished by including sources of the constituents of the zeolite in an aqueous reaction medium containing the template material and heating, generally, under elevated pressure until crystallisation has taken place. Very suitably the proportions of the sources of the constituents are such as to provide a reaction medium having the following composition in terms of oxide mole ratios.

$$\frac{SiO_2}{M_2O_3} = 6 \text{ to infinity preferably 10 to 200}$$

$$\frac{R_2O}{SiO_2} = 0 \text{ to } 1.0 \text{ preferably } 0.01 \text{ to } 0.7$$

$$\frac{Template}{SiO_2} = 0.01 \text{ to } 0.2 \text{ preferably } 0.02 \text{ to } 0.1$$

$$\frac{H_2O}{R_2O} = 50 \text{ to } 1000 \text{ preferably } 50 \text{ to } 800$$

where R, and M have the values above defined. Suitably, the alkali metal may be provided by the hydroxide and/or by the use of an alkali metal silicate; the $SiO_2$ may be provided by the use of a silica hydrosol or gel, by silicic acid or by said sodium silicate; and the metal M may be provided by the sodium metallate, for example, aluminate or by the use of a metallosilicate, for example aluminosilicate. Alternative sources of the desired ingredients will be well known to those versed in the art. Suitably, the synthesis may be carried out under alkaline conditions, at a temperature of from 100° C. to 300° C. and at a pressure of from about 1 to 100 bars which may, if desired, be generated autogenously. The zeolite so formed may be separated, washed free of residual reaction medium, dried and calcined to remove residual template materials and/or to reduce or remove water of crystallisation.

BRIEF DESCRIPTION OF THE DRAWINGS

FIG. I is an x-ray diffraction pattern obtained upon the product of the preparation I(a) obtained in the Example I.

FIG. II is the NMR spectra ($29_{si}$ MAS) obtained on the product of Preparation I(a) of Example I.

FIG. III is the isotherm for adsorption of isobutane on the product of Preparation I(a), Example I.

FIG. IV is an X-ray diffraction pattern of a novel zeolite of the invention.

FIG. V is an X-ray diffraction pattern of the product of synthesis (b) in Example I.

DETAILED DESCRIPTION OF THE INVENTION

Very many specific zeolite synthesis have been described in detail in the literature and many of these are summarised in the book "Molecular Sieves" by D. W. Breck (1974 John Wiley & Sons). A major characteristic of these syntheses is not the mole ratio of reactants, although this may to an extent be tailored to the type of zeolite required, but the particular organic template to be used to produce a desired zeolite type. British Pat. No. 1161974, for example, specifies the use of a tetrapropyl ammonium hydroxide template to produce zeolite ZSM5, the oxide mole ratios of reactions being specified very broadly as follows:

$SiO_2/Al_2O_3$: 20 to 60
$Na_2O/Al_2O_3$: at least 1
template/$Al_2O_3$: at least 1
$H_2O$/template+$Na_2O$: 5 to 50

British Pat. No. 1339501 describes the use of a cation of a quaternary compound of an element of group 5A of the Periodic Table, tetrabutyl ammonium and tetrabutyl phosphonium cations being particularly useful, as a template to produce zeolite ZSM11 the oxide mole ratios of reactants being specified as $SiO_2/Al_2O_3$: 10–150
$Na_2O/SiO_2$: 0.05 to 0.7
template/$SiO_2$: 0.02–2.0
$H_2O/Na_2O$: 50–800

The periodical publication "Zeolites" 1983 Vol 3, October, pages 282-291 discloses the role of organic molecules in molecular sieve synthesis and indicates as set out in Table I below the influence of templates in directing synthesis to certain structure types.

TABLE I

| ZSM-5 type | Omega-type |
|---|---|
| Tripropyl amine | Trimethyl amine |

TABLE I-continued

| | |
|---|---|
| Triethyl amine | Choline chloride |
| Tri-propylamine | Pyrrolidine |
| Ethylenediamine | |
| Ethanolamine | |
| Propanolamine | |
| Methylquinuclidine | |
| $NH_3$ + alcohol | |
| Alcohol | |
| Glycerol | |
| n-propylamine | |
| Di-n-butylamine | |
| Di-n-propylamine | |
| 1,5-diaminopentane | |
| 1,6-diaminohexane | |
| Morpholine | |
| Pentaerythritol | |
| Dipropylenetriamine | |
| Dihexamethylenetriamine | |
| Triethylenetetraamine | |
| Diethylenetriamine | |
| 1-alkyl, 4-aza, | |
| 1 azoniabicyclo(2,2,2)octane, | |
| 4-oxide, halide | |
| Hexanediol | |
| Propylamine | |

| Ferrierite-type | AlPO-5 type |
|---|---|
| Choline | Tetraethyl ammonium hydroxide |
| Pyrrolidine | Tetrapropyl ammonium hydroxide |
| Ethylene diamine | Choline hydroxide |
| | triethylamine |
| | tripropylamine |
| | $(CH_2CH_2OH)_3N$ |
| 1,3-diaminopropane | Cyclohexylamine |
| 1,4-diaminobutane | N,N'—dimethylbenzylamine |
| 2,4-pentanedione | Diethylethanolamine |
| N—methylpyridinium hydroxide | Amino diethylethanolamine |
| Piperidine and alkyl piperidine | Dimethylethanolamine |
| | Methyldiethanolamine |
| | Methylethanolamine |
| | 2-Picoline; 3-Picoline; 4-Picoline |
| | Diethypiperazine |
| | N—methylpiperidine |
| | 3-methylpiperidine |
| | N—methylcyclohexylamine |
| | Dicyclohexylamine |
| | Ethyl-n-butylamine |

The templates specifically disclosed above are substantially all non-optically active and incapable of existing as racemates. An exception to this is 3-methyl piperidine which is listed as being suitable for use in the synthesis of an aluminophosphate molecular sieve (ALPO-5). This compound exists as a racemate.

An enantiomer of 3-methyl piperidine may be prepared by separation from the racemate, for example by the process described in our copending European Patent Application claiming the same priority dates as the present application or by direct synthesis. The process of said European Patent Application is to utilise a crystalline molecular sieve having an assymetric crystal structure such as zeolite ZSM11, zeolite Theta I or silicalite II, the silica analogue of ZSM11, which are assymetric zeolites and may be prepared as described in British Pat. No. 1339501, European Patent Specification No. 0057049 and Nature Vol 280, Aug. 23, 1979 pages 664–665 respectively as a stereoselective adsorbent for one enantiomer of a racemate, the channels of the molecular sieve being partially blocked, when that molecular sieve is not itself enantiomorphic, by an enantiomer separable from those which constitute the racemate being adsorbed. By such means an eluate relatively concentrated in one enantiomer may be produced and the concentration thereof may be increased as required by recycling.

Examples of other enantiomers which may be used according to the present invention are compounds belonging to the groups quaternary ammonium compounds, amines, alcohols, and heterocyclic compounds and may be selected, for example, from the list of chiral building blocks on pages 1067 to 1069 of the FLUKA (Fluorochem Limited) Catalogue No. 14, 1984–5, for example alphapinene, 2 methyl butanol or piperidium compounds such as the 3-methyl piperidine-N,N-dimethyl cation or a cobalt interpenetration complex as $Co^{+3}$ bis(ethylene diamine) or other $Co^{+3}$ complexes with low molecular weight ligands containing for example not more than 4 carbon atoms.

There is a growing need for more, or relatively concentrated, enantiomers which, although they may be common in nature are often produced in the racemic form by synthesis. One method for achieving the required separation is by stereoselective adsorption of one enantiomer onto an assymetric crystalline molecular sieve as disclosed above.

It is postulated that the zeolites produced by the present invention may be assymetric either in the sense of possessing two sets of pores of opposite symmetry, or in the sense of being enantiomeric and that, if so, they may exhibit chiral adsorption properties relative to racemic mixtures.

EXAMPLE I

A normal ZSM11 type reaction mixture as described in U.S. Pat. No. 4,108,881 modified by the use of the new template was used herein. The reaction mixture mixed in 20 ml capacity PTFE lined bombs and heated for 165 hours at 165° C.

Order of addition
13.7 g water
0.2 g sodium aluminate (20% w/w $Na_2O$) (25% w/w $Al_2O_3$)
0.28 g sodium hydroxide pellets
1.6 g template
8.1 g Ludox (Trade Mark) LS30 (30% w/w $SiO_2$).

The templates used were as follows in two preparations I(a) and I(b):
(a) N,N-dimethyl-3-S-(—)-methyl piperidinium bromide
(b) N,N-dimethyl-3-S-(—)-methyl piperidinium iodide The templates may be synthesised using known methods—see for example "Optical Resolution Procedures for Chemical Compounds" Vol 1) by Paul Newman of the Optical Resolution Information Centre, Manhattan College, Riverdale, N.Y. 10471.

The product of preparation (a) had oxide ratios indicated by the following chemical analysis $Al_2O_3$: 2.24%
$SiO_2$: 96.8
$K_2O$: 0.01
BaO: 0.01
CaO: 0.01
$TiO_2$: 0.02
$Fe_2O_3$: 0.01
SrO: 0.01
MgO: 0.05
$Na_2O$: 0.57
Total: 99.6 and an x-ray diffraction pattern as indicated in FIG. I attached and having peaks at the following spacings.

XRD Trace 3–45 degrees

Major: PEAKS at ca 20, 11.6, 10.9, 9.8, 9.1, 7.5, 6.8, 5.8, 4.62.

Minor: 4.46, 4.31 (S), 3.98, 3.83, 3.77, 3.69, 3.57, 3.45, 3.35, 3.

Trace: 28, 3.23, 3.12, 3.08, 3.01, 2.90, 2.84, 2.74, 2.69, 2.51.

Slight Trace: 2.45, 2.42, 2.39, 2.31, 2.19, 2.10 and 2.03A.

and $^{29}$Si spectra by magic angle spinning nuclear magnetic resonance spectroscopy ($^{29}$Si MAS) after calcination at 450° C. indicated by FIG. II attached hereto.

Product (a) gave the isotherm for adsorption of isobutane shown in FIG. III attached hereto.

The above data indicate a zeolite structure and the x-ray diffraction and spectroscopy data indicate the presence of ZSM12 (identified in British patent specification No. 1365317) and an unidentified material. Refluxing 0.5 g of product per 10 ml of 0.5 moles of dm$^3$ concentration NaOH for one hour resulted in a material giving the x-ray diffraction pattern shown in FIG. IV from which the ZSM12 peaks are missing and which is believed to be a new zeolite. The new material has a composition, expressed in terms of wt % of oxides, of 0%–10% $Al_2O_3$, 86%–100% $SiO_2$, trace amounts not more than 0.2% in total of one or more of $K_2O$, BaO, CuO, $TiO_2$, $Fe_2O_3$, SrO, MgO and 0 to 4% $Na_2O$.

The product of synthesis (b) was also subjected to x-ray diffraction to give the trace shown in FIG. V containing both the characteristic peaks of mordenite, those of zeolite ZSM 12 and some unidentified peaks and is therefore deduced to be a mixture containing ZSM 12. Its chemical analysis is:

$Al_2O_3$: 3.03%
$SiO_2$: 94.6
$K_2O$: 0.18
BaO: 0.01
CaO: 0.01
$TiO_2$: 0.06
$Fe_2O_3$: 0.10
SrO: 0.01
MgO: 0.03
$Na_2O$: 1.24
Total: 99.2

When this product was refluxed with 1.0 mole/dm$^{-3}$ concentration NaOH for four hours 40% of the product was dissolved and the remaining material gave an x-ray diffraction pattern of X2 phase silica. Refluxing with 0.1 mol/dm$^{-3}$ NaOH for 1 hour gave a material giving an x-ray diffraction pattern which showed reductions in peaks characteristic of mordenite and of ZSM12. This material was examined by scanning election microscopy and it was shown that several crystal structures were present some being identifiable as being similar to mordenite and some to quartz. The results are interpreted as indicating that the product (b) was a mixture of X2 phase silica, ZSM12 and mordenite.

I(c)

In this preparation the same conditions were used except that the template was racemic 3-methyl piperidine-N,N dimethyl bromide.

The product was a crystalline material giving an x-ray diffraction pattern and oxide mole ratios corresponding to zeolite ZSM12.

We claim:

1. A process for the production of a synthetic crystalline molecular sieve material by the use of a reaction mixture containing an organic template material characterised in that the template is an enantiomer.

2. A process as claimed in claim 1 wherein the template is an amine or ammonium enantiomer.

3. A process as claimed in claim 2 wherein the template is an piperidine enantiomer.

4. A process as claimed in claim 1 for the production of a crystalline high silica zeolite molecular sieve comprising forming an aqueous reaction mixture containing a template comprising an enantiomer and sources of $R_2O$, $SiO_2$ and optionally $M_2O_3$ in the molar proportions $$\frac{SiO_2}{M_2O_3} = 6 \text{ to infinity}$$

$$\frac{R_2O}{SiO_2} = 0 \text{ to } 0.7$$

$$\frac{Template}{SiO_2} = 0.01 \text{ to } 0.2$$

$$\frac{H_2O}{R_2O} = 50 \text{ to } 1000$$

wherein R indicates an alkali metal and M indicates one or more metals selected from B, Al, V, Cr, Mr, Fe, Ga, As, Mo or Sb, hydrothermally treating the reaction mixture at a temperature of from 100° C. to 300° C. and a pressure of from 1 to 100 bars until crystallisation occurs and separating the crystalline product so formed.

5. A process as claimed in claim 4 wherein the molar proportions of the reactants are $$\frac{SiO_2}{M_2O_3} = 10 \text{ to } 150$$

$$\frac{R_2O}{SiO_2} = 0.5 \text{ to } 0.7$$

$$\frac{Template}{SiO_2} = 0.02 \text{ to } 2.0$$

$$\frac{H_2O}{R_2O} = 50 \text{ to } 800$$

and R is Na and M is Al.

* * * * *